United States Patent [19]

Wood et al.

[11] Patent Number: 5,498,425
[45] Date of Patent: Mar. 12, 1996

US005498425A

[54] PHOSPHOSODA BUFFERED SALINE LAXATIVE

[75] Inventors: Thomas G. Wood, Morris Plains; Frederick A. Curro, Emerson, both of N.J.; Demetra E. Parashos, Flushing, N.Y.

[73] Assignee: Block Drug Company, Inc., Jersey City, N.J.

[21] Appl. No.: 405,959

[22] Filed: Mar. 17, 1995

[51] Int. Cl.⁶ .................................................. A61K 31/74
[52] U.S. Cl. ..................... 424/464; 424/78.01; 514/892
[58] Field of Search .................. 424/78.01, 401, 424/464; 514/892

[56] References Cited

U.S. PATENT DOCUMENTS

| | | | |
|---|---|---|---|
| 182,542 | 4/1876 | Yewell | 424/125 |
| 220,794 | 10/1879 | Bissell | 424/606 |
| 455,103 | 3/1891 | Hübener | 426/590 |
| 1,858,905 | 3/1932 | Rumanceff | 424/606 |
| 3,105,792 | 10/1963 | White | 424/44 |
| 3,936,385 | 2/1976 | Cheng | 252/99 |
| 4,115,307 | 9/1978 | McGilvery | 252/135 |
| 4,664,915 | 5/1987 | Simonian | 424/606 |
| 4,965,072 | 10/1990 | Alexander et al. | 424/458 |

OTHER PUBLICATIONS

National Formulary, National Formulary Board, 14th edition, 1975, pp. 654–656.
National Formulary, National Formulary Board, 18th edition, 1995, p. 1430.

Primary Examiner—Thurman K. Page
Assistant Examiner—Sharon Howard
Attorney, Agent, or Firm—Ostrolenk, Faber, Gerb & Soffen

[57] ABSTRACT

A laxative composition in powder or tablet form, having a pleasant odor and taste. The composition comprises sodium bicarbonate, monobasic sodium phosphate in stoichiometric excess, and a pineapple flavoring composition containing also Magnasweet 185 and sodium saccharin. A minor amount of citric or malic acid may be present.

5 Claims, No Drawings

PHOSPHOSODA BUFFERED SALINE LAXATIVE

BACKGROUND OF THE INVENTION

Purgatives (laxatives or cathartics) are widely used as self medications to satisfy the patient's desire for an altered or more regular bowel habit. They are also used for bowel clearance before radiological examination, surgery, or childbirth. Purgatives used in the treatment of functional constipation include phenolphthalein, senna, cascara, bisacodyl, and sodium picosulfate. Salts of inorganic acids which are not extensively absorbed from the gastrointestinal tract, such as sodium phosphate, retain water in the lumen of the bowel by an osmotic effect and are also used as purgatives. Prolonged use of purgatives may produce excessive loss of water and electrolytes, particularly potassium. A commonly used oral lavage solution is Fleet's concentrated phosphosoda solution which is manufactured according to the National Formulary monograph for Sodium Phosphates Oral Solution. This product, as described in the National Formulary (USP 23/NF 18, p. 1430), contains disbasic sodium phosphate and monobasic sodium phosphate or phosphoric acid in water. The marketed product, which claims a ginger-lemon flavor, in fact, has a very strong salty and sour taste. No other flavoring is evident, even as an aftertaste.

SUMMARY OF THE INVENTION

The present invention provides a laxative composition having a pleasant odor and taste. The composition comprises sodium bicarbonate, monobasic sodium phosphate and a pineapple flavoring, the monobasic sodium phosphate being present in stoichiometric excess. The pineapple flavoring composition contains pineapple flavor, Magnasweet 185 and sodium saccharin. A minor proportion of citric or malic acid may be present. The composition may be in powder dosage form or in the form of a tablet.

DETAILED DESCRIPTION OF THE INVENTION

The present invention utilizes the reaction of monobasic sodium phosphate monohydrate and sodium bicarbonate in water to produce dibasic sodium phosphate monohydrate, carbon dioxide (which dissipates) and water, according to the following equation:

$$NaHCO_3 + NaH_2PO_4 \rightarrow Na_2HPO_4 + CO_2 + H_2O$$

An excess of monobasic sodium phosphate monohydrate is used to react with a calculated amount of sodium bicarbonate so that with the addition of water the amount of dibasic sodium phosphate required by the NF Monograph for Sodium Phosphate Oral Solution is produced. The reaction product is a buffer system of monobasic sodium phosphate and dibasic sodium phosphate. A non-gas producing powder pineapple flavoring formula is added. All components are in powder form and are mixed well together, so that a homogeneous mixture ensures before the addition of water. The final solution has a pleasant odor and taste.

A laxative dose suitably consists of 126 g $NaH_2PO_4 \cdot H_2O$ 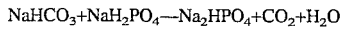 and 1.27 g $NaHCO_3$. A patient is required to take twice the laxative dose for purgative purposes. The product can be marketed as is, in powder form, or, if mixed with tableting excipients, as a tablet.

The reaction of sodium bicarbonate with excess monobasic sodium phosphate will produce the dibasic sodium phosphate in the amount described by the N. F. monograph. A major advantage over the N. F. monograph formulation is the taste of the present formulation. Masking of the salty taste of the unflavored formulation is complete. When the reaction with water is complete, a pleasant tasting pineapple drink is the final product.

The flavoring system used here, is a non-gas producing formula, an important factor for use of the product as a purgative.

The following examples are illustrative of the composition of this invention:

EXAMPLE 1

PHOSPHOSODA BUFFERED SALINE LAXATIVE FORMULA (per dose)

| Ingredients | Amount (g/dose) | Percent |
| --- | --- | --- |
| 1) Monobasic Sodium Phosphate Monohydrate | 12.6 | 86.9 |
| 2) Sodium Bicarbonate | 1.3 | 8.96 |
| 3) Pineapple Flavor | 0.25 | 1.72 |
| 4) Magnasweet 185 | 0.3 | 2.07 |
| 5) Sodium Saccharin Dihydrate (U.S.P.) | 0.05 | 0.34 |

Magnasweet 185 is a sweetening composition based on glycyrrhizic acid, available from McAndrews and Forbes Co., Camden, N.J.

EXAMPLE 2

POWDER PACKET

A powder packet was prepared as follows:

(1) Ingredients (1) and (2) were blended together using a mortar and pestle.

(2) Ingredients (3), (4) and (5) were blended together using a different mortar and pestle.

(3) The flavoring mixture, i.e. pineapple flavor, Magnasweet 185 and sodium saccharine dihydrate blend from Step (2), was then added to the mortar that contained the salt blend from Step 1 and everything was blended together.

In use, the final formula is added to 8.0 oz. of water (120 ml), as required for the laxative dose. Effervescence starts immediately, and with a little stirring the reaction goes to completion within two minutes. Slight mixing, as by a teaspoon, speeds the reaction.

To prepare the composition of this invention in effervescent tablet form, ingredients (1) through (5) are blended with tableting excipients appropriate for effervescent tablets. A binder to help cohesion of the individual ingredients and a lubricant to help compression and speed production, are both necessary for a successful tablet formulation. Lubricants that can be used are: sodium lauryl sulfate, micronized polyethylene glycol 8000, stearic acid and its magnesium and calcium salts, sodium benzoate, sterotax and polyvinylpyrrolidone. Binders that can be used include pregelatinized starch, sugar-tab, granular di-pak and polyvinylpyrrolidone. In the absence of a suitable binder, ingredients (1) and (2) can be manipulated by wet granulation or cohesion through heating to help the binding of the tablet. Inert excipient like binders and lubricants may affect the effervescence of the tablet. A small quantity of an edible organic acid such as citric or malic acid may be used to help initiate the reaction with sodium bicarbonate.

The effervescent tablets and powders may be packaged in aluminum lined paper containers. Such packets are economical and easier to ship, store and generally handle than plastic bottles filled with solution that one still has to dilute.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A laxative composition comprising sodium bicarbonate, monobasic sodium phosphate and a pineapple flavoring, the monobasic sodium phosphate being present in stoichiometric excess, and said pineapple flavoring comprising pineapple flavor, glycyrrhizic acid and sodium saccharin.

2. A composition of claim 1, wherein citric or malic acid is present.

3. A composition of claim 1 in powder dosage form.

4. A composition of claim 1 in the form of a tablet.

5. A composition of claim 2 in the form of a tablet.

\* \* \* \* \*